(12) United States Patent
Myers et al.

(10) Patent No.: US 6,440,476 B2
(45) Date of Patent: Aug. 27, 2002

(54) METHOD TO IMPROVE QUALITY AND APPEARANCE OF LEAFY VEGETABLES BY USING STABILIZED BROMINE

(75) Inventors: Eric R. Myers; Anthony W. Dallmier, both of Aurora, IL (US)

(73) Assignee: Nalco Chemical Company, Naperville, IL (US)

( * ) Notice: Subject to any disclaimer, the term of this patent is extended or adjusted under 35 U.S.C. 154(b) by 92 days.

(21) Appl. No.: 09/752,339

(22) Filed: Dec. 29, 2000

Related U.S. Application Data

(63) Continuation-in-part of application No. 09/304,724, filed on May 4, 1999, now abandoned, which is a continuation-in-part of application No. 08/904,375, filed on Aug. 1, 1997, now Pat. No. 5,942,126, which is a continuation-in-part of application No. 08/778,598, filed on Jan. 3, 1997, now Pat. No. 5,795,487.

(51) Int. Cl.[7] ............................................... A23C 7/157
(52) U.S. Cl. ................... 426/335; 426/321; 426/532; 426/615; 426/654
(58) Field of Search ................... 426/335, 532, 426/321, 615, 654

(56) References Cited

U.S. PATENT DOCUMENTS

| | | |
|---|---|---|
| 3,170,883 A | 2/1965 | Owen et al. |
| 3,328,294 A | 6/1967 | Self et al. |
| 3,558,503 A | 1/1971 | Goodenough et al. |
| 3,749,672 A | 7/1973 | Golton et al. |
| 3,767,586 A | 10/1973 | Rutkiewic |
| 4,096,029 A | 6/1978 | Mills |
| 4,241,080 A | 12/1980 | Burk |
| 4,451,376 A | 5/1984 | Sharp |
| 4,642,194 A | 2/1987 | Johnson |
| 4,693,894 A | 9/1987 | Juda et al. |
| 4,711,724 A | 12/1987 | Johnson |
| 4,759,852 A | 7/1988 | Trulear |
| 4,929,424 A | 5/1990 | Meier et al. |
| 4,992,209 A | 2/1991 | Smyk et al. |
| 5,076,952 A | 12/1991 | Ahmed et al. |
| 5,112,530 A | 5/1992 | Bauer et al. |
| 5,424,032 A | 6/1995 | Christensen et al. |
| 5,476,670 A | 12/1995 | Hight et al. |
| 5,525,241 A | 6/1996 | Clavin |
| 5,641,520 A | 6/1997 | Howarth et al. |
| 5,662,940 A | 9/1997 | Hight et al. |

FOREIGN PATENT DOCUMENTS

| | | |
|---|---|---|
| AU | 77338/87 | 3/1988 |
| GB | 1475570 A | 6/1977 |
| WO | 97/20909 | 6/1997 |
| WO | 97/34827 A | 9/1997 |

*Primary Examiner*—Helen Pratt
(74) *Attorney, Agent, or Firm*—Maragret M. Brumm; Thomas M. Breininger

(57) ABSTRACT

A method to extend the shelf-life, reduce the microbial load, and enhance product appearance and quality in leafy vegetables or other fresh commodities of the like comprising applying directly to the leafy vegetable a stabilized aqueous alkali or alkaline earth metal hypobromite solution.

8 Claims, No Drawings

METHOD TO IMPROVE QUALITY AND APPEARANCE OF LEAFY VEGETABLES BY USING STABILIZED BROMINE

CROSS-REFERENCE TO RELATED PATENT APPLICATIONS

This application is a continuation-in-part of U.S. patent application Ser. No. 09/304,724, filed May 4, 1999, abandoned; which is a continuation-in-part of U.S. patent application Ser. No. 08/904,375, filed Aug. 1, 1997 (now U.S. Pat. No. 5,942,126), which is a continuation-in-part of U.S. patent application Ser. No. 08/778,598, filed Jan. 3, 1997 (now U.S. Pat. No. 5,795,487).

FIELD OF THE INVENTION

The present invention is in the field of treatment of leafy vegetables or other fresh commodities in general. Specifically the invention is in the field of treating leafy vegetables to enhance their product shelf life, reduce microbial loading, and improve product appearance and quality.

BACKGROUND OF THE INVENTION

Leafy vegetables or other fresh commodities are typically treated with aqueous solutions of sodium hypochlorite, also known as bleach. This treatment is conducted to enhance the product shelf life and maintain product quality. Because of the desirability of reducing the amount of chlorine introduced into the environment, it would be desirable to have an alternative treatment to enhance product appearance and shelf life in leafy vegetables or other fresh commodities.

SUMMARY OF THE INVENTION

The instant claimed invention is a method to extend the shelf-life, reduce the microbial load, and enhance product appearance and quality in leafy vegetables comprising applying directly to the leafy vegetable or other fresh commodities of the like a stabilized aqueous alkali or alkaline earth metal hypobromite solution.

DETAILED DESCRIPTION OF THE INVENTION

The following terms have the indicated meanings:

"APC" refers to aerobic plate count bacteria

"CFU" refers to colony forming units.

"YM" refers to yeast and mold count

The instant claimed invention is a method to extend the shelf-life, reduce the microbial load, and enhance product appearance and quality in leafy vegetables comprising applying directly to the leafy vegetable or other fresh commodities of the like a stabilized aqueous alkali or alkaline earth metal hypobromite solution.

Stabilized aqueous alkali or alkaline earth metal hypobromite solutions are commercially available under the trademark STA-BR-EX® from Nalco Chemical Company, One Nalco Center, Naperville, Ill. 60563, (630) 305–1000. These solutions of stabilized aqueous alkali or alkaline earth metal hypobromite typically contain from about 1 to about 30 percent by weight alkali or alkaline earth metal hypobromite. Preferably these solutions contain from about 4 to about 15 percent by weight alkali or alkaline earth metal hypobromite.

The pH of the stabilized aqueous alkali or alkaline earth metal hypobromite solution is from about 8 to about 14, preferably from about 11 to about 14.

Leafy vegetables are selected from the group consisting of leaf lettuce, head lettuce, spinach, cauliflower, broccoli, celery, cabbage, or the like. The preferred leafy vegetable is leaf lettuce.

The method of applying a stabilized aqueous alkali or alkaline earth metal hypobromite solution to the leafy vegetable or any other commodity of interest is conducted by applying the solution directly to the leafy vegetable. There are many methods of applying solutions to leafy vegetables that are known to people of ordinary skill in the art of leafy vegetables or any other commodity of interest. The preferred way of doing this is to fully immerse the entire leafy vegetable into a solution of stabilized aqueous alkali or alkaline earth metal hypobromite. The application time, also known as the immersion time, is from about 5 seconds to about 7 minutes, preferably from about 5 seconds to about 5 minutes, and most preferably from about 5 seconds to about 3 and a half minutes and most highly preferably about 3 minutes.

The solutions of stabilized aqueous alkali or alkaline earth metal hypobromite applied directly to said leafy vegetables in an amount of from about 0.05 to about 5,000 ppm total available halogen as chlorine, preferably from about 2 to about 200 ppm total available halogen as chlorine.

Leafy vegetables treated with solutions of stabilized aqueous alkali or alkaline earth metal hypobromite have a shelf life and appearance similar to those leafy vegetables treated with bleach (sodium hypochlorite). Therefore, the application of stabilized aqueous alkali or alkaline earth metal hypobromite to leafy vegetables is a viable alternative treatment to the standard treatment of leafy vegetables with a chlorine based material.

The following examples are presented to describe preferred embodiments and utilities of the invention and are not meant to limit the invention unless otherwise stated in the claims appended hereto.

EXAMPLES

Direct Application of Stabilized Sodium Hypobromite Solution to Leaf Lettuce to Improve Shelf-life.

Solutions of either stabilized sodium hypobromite or industrial unstabilized sodium hypochlorite were added to "tap" water in order to achieve a 50, 100, or 200 ppm total halogen residual (as chlorine). The "tap" water contained calcium (90 ppm as $CaCO_3$), "M" alkalinity (110 ppm as $CaCO_3$) and magnesium (50 ppm as $CaCO_3$) in deionized water. The "tap" water was buffered at pH 7.5 using borax and monobasic potassium phosphate. Solutions of stabilized sodium hypobromite or unstabilized sodium hypochlorite were applied directly to leaf lettuce by dipping the lettuce in the solutions for 3-minutes. Lettuce was immediately removed, drained for 1-minute, rinsed for 30-seconds with potable water, drained for 1-minute, and then spun dry with a bench-top lettuce spinner. Lettuce was analyzed for microbial populations remaining on the surface and 50-gram portions were stored at 4–6° C. for shelf-life evaluation. Shelf-life was visually judged for changes in color (browning) and odor.

Reduction of microbial populations after direct application of a halogen solution is summarized in Tables 1a and 1b.

TABLE 1a

Log reduction of microbial populations from leaf lettuce surface. Reductions were compared to unwashed control.

| | Control | | STABREX ® (ppm av. $Cl_2$) | | | Bleach (ppm av. $Cl_2$) | | |
|---|---|---|---|---|---|---|---|---|
| | Unwashed | Washed | 50 | 100 | 200 | 50 | 100 | 200 |
| APC | 0.0 | 0.0 | 2.1 | 2.0 | 2.1 | 2.1 | 2.1 | 2.1 |
| YM | 0.0 | −0.6 | 1.2 | 1.2 | 1.0 | 2.4 | 2.3 | 2.5 |

TABLE 1b

Percent reduction of microbial populations from leaf lettuce surface. Reductions were compared to unwashed control.

| | Control | | STABREX ® (ppm av. $Cl_2$) | | | Bleach (ppm av. $Cl_2$) | | |
|---|---|---|---|---|---|---|---|---|
| | Unwashed | Washed | 50 | 100 | 200 | 50 | 100 | 200 |
| APC | 0.000 | 0.000 | 99.160 | 99.040 | 99.200 | 99.200 | 99.120 | 99.200 |
| YM | 0.000 | −252.941 | 94.706 | 93.529 | 90.588 | 99.647 | 99.494 | 97.729 |

Aerobic bacteria were reduced about 2-orders of magnitude when any of the halogen solutions were directly applied to the lettuce compared to only washing with water, which did not show any reduction. Yeasts and molds were reduced by one-log when washed with stabilized sodium hypobromite compared to bleach, which reduced the yeasts and molds by about 2-logs. Microbiologically, stabilized sodium hypobromite is comparable to bleach.

Tables 2 and 3 show the aerobic plate count (APC) bacteria and the yeast and mold (YM) count populations on the lettuce during storage at 4–6° C., respectively.

TABLE 2

Aerobic plate count (APC) bacterial populations ($Log_{10}$ CFU/g lettuce) on leaf lettuce during storage at 4–6° C. Bolded numbers indicate when the lettuce was judged unacceptable.

| | Control | | STABREX ® (ppm av. $Cl_2$) | | | Bleach (ppm av. $Cl_2$) | | |
|---|---|---|---|---|---|---|---|---|
| Day | Unwashed | Washed | 50 | 100 | 200 | 50 | 100 | 200 |
| 0 | 7.4 | 7.4 | 5.3 | 5.4 | 5.3 | 5.3 | 5.3 | 5.3 |
| 1 | 7.3 | 7.2 | 5.8 | 5.6 | 5.5 | 5.4 | 5.3 | 5.5 |
| 2 | 8.3 | 7.4 | 6.9 | 6.2 | 6.6 | 6.4 | 6.6 | 7.0 |
| 4 | 8.0 | 7.3 | 6.5 | 6.2 | 6.7 | 6.5 | 6.6 | 7.5 |
| 5 | 7.9 | 7.0 | 7.1 | 6.0 | 7.1 | 6.0 | 6.4 | 6.6 |
| 6 | 7.5 | 7.8 | 7.7 | 6.4 | 7.2 | 6.6 | 6.6 | 8.1 |
| 7 | 7.6 | 8.4 | 8.0 | 7.7 | 7.8 | 7.2 | 7.2 | 7.7 |
| 8 | 7.7 | 8.4 | 7.4 | 7.6 | 7.7 | 7.7 | 8.1 | 7.6 |
| 9 | 7.8 | 8.7 | 8.3 | 8.7 | 7.6 | 7.6 | 7.4 | 7.5 |
| 10 | 7.6 | 8.1 | 7.9 | 8.5 | 8.2 | 7.6 | 7.0 | 8.6 |
| 11 | 7.8 | 8.2 | 8.1 | 8.4 | 8.2 | 8.0 | 7.9 | 8.5 |
| 12 | 7.9 | 9.1 | 8.9 | 8.1 | 9.0 | 8.3 | 8.0 | 8.4 |

TABLE 3

Yeast and mold (YM) count populations ($Log_{10}$ CFU/g lettuce) on leaf lettuce during storage at 4–6° C. Bolded numbers indicate when the lettuce was judged unacceptable.

| | Control | | STABREX ® (ppm av. $Cl_2$) | | | Bleach (ppm av. $Cl_2$) | | |
|---|---|---|---|---|---|---|---|---|
| Day | Unwashed | Washed | 50 | 100 | 200 | 50 | 100 | 200 |
| 0 | 5.2 | 5.8 | 4.0 | 4.0 | 4.2 | 2.8 | 2.9 | 2.7 |
| 1 | 5.8 | 6.1 | 4.3 | 4.2 | 4.0 | 2.7 | 2.9 | 2.7 |

TABLE 3-continued

Yeast and mold (YM) count populations ($Log_{10}$ CFU/g lettuce) on leaf lettuce during storage at 4–6° C. Bolded numbers indicate when the lettuce was judged unacceptable.

| | Control | | STABREX ® (ppm av. $Cl_2$) | | | Bleach (ppm av. $Cl_2$) | | |
|---|---|---|---|---|---|---|---|---|
| Day | Unwashed | Washed | 50 | 100 | 200 | 50 | 100 | 200 |
| 2 | 5.9 | 6.0 | 4.3 | 4.4 | 4.2 | 2.7 | 2.8 | 2.8 |
| 4 | 5.6 | 5.8 | 3.3 | 3.5 | 3.0 | 4.5 | 4.1 | 4.4 |
| 5 | 5.1 | 6.2 | 4.5 | 4.1 | 4.4 | 3.3 | 3.5 | 3.0 |
| 6 | 5.7 | 6.0 | 5.1 | 4.6 | 4.7 | 3.8 | 3.9 | 4.5 |
| 7 | 5.7 | 5.2 | 5.1 | 5.2 | 4.8 | 3.7 | 4.5 | 4.0 |
| 8 | 5.9 | 5.8 | 4.9 | 5.0 | 4.6 | 4.4 | 4.9 | 4.4 |
| 9 | 5.7 | 6.3 | 5.4 | 5.5 | 4.8 | 4.0 | 4.6 | 4.2 |
| 10 | 5.6 | 5.5 | 5.3 | 5.6 | 5.1 | 4.1 | 3.8 | 4.5 |
| 11 | 5.7 | 5.8 | 5.5 | 5.4 | 5.5 | 4.9 | 4.5 | 4.6 |
| 12 | 5.8 | 5.9 | 5.3 | 5.3 | 5.4 | 5.5 | 4.8 | 4.8 |

During storage, the populations increased. Numbers in bold indicate the time in which the product was judged unacceptable (Tables 3 and 4). Although the microbial populations do not indicate definitively when the lettuce becomes unacceptable, the data do indicate microbial activity. Microbial activity accelerates or contributes to deterioration or spoilage of the lettuce.

After lettuce was washed by direct application of a halogen solution, the shelf-life of the lettuce was observed at 4–6° C. Lettuce was considered unacceptable if noticeable off-odors were noted and if significant browning or darks sports were present. Based on the odor and dark spot sensory scores, lettuce was given a pass or fail rating (Table 4). Unwashed lettuce had a shelf-life of about nine days, which was comparable to stabilized aqueous alkali or alkaline earth metal hypobromite solution and bleach applied at 100 and 200 pm as total available chlorine. If lettuce was washed with only water, its shelf-life was about 7-days. Since water is used to process lettuce, and water washed lettuce is know to deteriorate sooner than unwashed lettuce, direct application of a halogen solution should allow an equivalent shelf-life to unwashed lettuce.

TABLE 4

Sensory rating (PASS/FAIL) of leaf lettuce during storage at 4–6° C.

| | Control | | STABREX ® (ppm av. Cl$_2$) | | | Bleach (ppm av. Cl$_2$) | | |
| --- | --- | --- | --- | --- | --- | --- | --- | --- |
| Day | Unwashed | Washed | 50 | 100 | 200 | 50 | 100 | 200 |
| 0 | PASS | PASS | PASS | PASS | PASS | PASS | PASS | PASS |
| 1 | PASS | PASS | PASS | PASS | PASS | PASS | PASS | PASS |
| 2 | PASS | PASS | PASS | PASS | PASS | PASS | PASS | PASS |
| 4 | PASS | PASS | PASS | PASS | PASS | PASS | PASS | PASS |
| 5 | PASS | PASS | PASS | PASS | PASS | PASS | PASS | PASS |
| 6 | PASS | PASS | PASS | PASS | PASS | PASS | PASS | PASS |
| 7 | PASS | PASS | PASS | PASS | PASS | PASS | PASS | PASS |
| 8 | PASS | FAIL | PASS | PASS | PASS | PASS | PASS | PASS |
| 9 | PASS | FAIL | FAIL | PASS | PASS | FAIL | PASS | PASS |
| 10 | FAIL | FAIL | FAIL | FAIL | FAIL | FAIL | FAIL | FAIL |
| 11 | FAIL | FAIL | FAIL | FAIL | FAIL | FAIL | FAIL | FAIL |
| 12 | FAIL | FAIL | FAIL | FAIL | FAIL | FAIL | FAIL | FAIL |

The above examples demonstrate that the direct application of stabilized aqueous alkali or alkaline earth metal hypobromite solution to lettuce is equivalent to bleach, and it is an excellent chlorine alternative. The stabilized sodium hypobromite has the additional benefits of increased safety in application, greater stability, and less volatility than sodium hypochlorite and other chlorine compounds.

Changes can be made in the composition, operation and arrangement of the method of the present invention described herein without departing from the concept and scope of the invention as defined in the following claims:

What is claimed is:

1. A method to extend the shelf-life, reduce the microbial load, and enhance product appearance and quality in leafy vegetables comprising applying directly to the leafy vegetable or other fresh commodities a stabilized aqueous alkali or alkaline earth metal hypobromite solution.

2. The method of claim 1 where said leafy vegetable is lettuce.

3. The method of claim 1 wherein said solution of stabilized aqueous alkali or alkaline earth metal hypobromite contains from about 1 to about 30 percent by weight alkali or alkaline earth metal hypobromite.

4. The method of claim 1 wherein said solution of stabilized aqueous alkali or alkaline earth metal hypobromite contains from about 4 to about 15 percent by weight alkali or alkaline earth metal hypobromite.

5. The method of claim 1 wherein the pH of the stabilized aqueous alkali or alkaline earth metal hypobromite solution is from about 8 to about 14.

6. The method of claim 1 wherein the pH of the stabilized aqueous alkali or alkaline earth metal hypobromite solution is from about 11 to about 14.

7. The method of claim 1 wherein the stabilized aqueous alkali or alkaline earth metal hypobromite solution is applied directly to said leafy vegetable in an amount of from about 0.05 to about 5,000 ppm total available halogen as chlorine.

8. The method of claim 1 wherein the stabilized aqueous alkali or alkaline earth metal hypobromite solution is applied directly to said leafy vegetable in an amount of from about 2 to about 200 ppm total available halogen as chlorine.

* * * * *